(12) United States Patent
Nagamoto et al.

(10) Patent No.: US 10,799,721 B2
(45) Date of Patent: *Oct. 13, 2020

(54) PARTICLE BEAM THERAPY APPARATUS

(71) Applicants: KABUSHIKI KAISHA TOSHIBA, Minato-ku (JP); Toshiba Energy Systems & Solutions Corporation, Kawasaki-shi (JP)

(72) Inventors: Yoshifumi Nagamoto, Yokohama (JP); Kiyohiko Kitagawa, Yokohama (JP); Kazutaka Maeta, Yokohama (JP)

(73) Assignees: KABUSHIKI KAISHA TOSHIBA, Minato-ku (JP); Toshiba Energy Systems & Solutions Corporation, Kawasaki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/437,375

(22) Filed: Jun. 11, 2019

(65) Prior Publication Data
US 2019/0308034 A1 Oct. 10, 2019

Related U.S. Application Data

(63) Continuation of application No. 15/763,634, filed as application No. PCT/JP2016/078762 on Sep. 29, 2016, now Pat. No. 10,363,438.

(30) Foreign Application Priority Data

Sep. 30, 2015 (JP) .................................. 2015-192811

(51) Int. Cl.
*A61N 5/10* (2006.01)
*A61B 6/10* (2006.01)
(Continued)

(52) U.S. Cl.
CPC .......... *A61N 5/1049* (2013.01); *A61B 6/0442* (2013.01); *A61B 6/102* (2013.01);
(Continued)

(58) Field of Classification Search
CPC ...... A61N 5/1049; A61N 5/10; A61N 5/1078; A61N 2005/1061; A61N 2005/1087; A61B 6/4007; A61B 6/4266; A61B 6/4452
(Continued)

(56) References Cited

U.S. PATENT DOCUMENTS 10,363,438 B2 * 7/2019 Nagamoto ............. A61B 6/587
2006/0163495 A1 7/2006 Hiramoto et al.
(Continued)

FOREIGN PATENT DOCUMENTS

CN    102026681 A    4/2011
EP    3 251 600 A1   12/2017
(Continued)

OTHER PUBLICATIONS

International Preliminary Report on Patentability and Written Opinion dated Apr. 3, 2018 in PCT/JP2016/078762.

*Primary Examiner* — Nicole M Ippolito
(74) *Attorney, Agent, or Firm* — Oblon, McClelland, Maier & Neustadt, L.L.P.

(57) ABSTRACT

A particle beam therapy apparatus 10 includes: a particle beam irradiator 16 outputting a particle beam B; a movable supporting structure 21 supporting the particle beam irradiator 16; movable plates 37 disposed on a displacement trajectory of the particle beam irradiator 16, forming a substantially horizontal enveloping surface below a table 18 for placing an irradiation object 13, and including first and second floor members in at least one of the movable plates 37, the second floor member being larger in X-ray trans- (Continued)

mittance than the first floor member; an X-ray generator 27*a* provided in a non-collision area 31 where the X-ray generator 27*a* does not collide with any of the particle beam irradiator 16, the supporting structure 21, and the movable plates 37; and an X-ray detector 27*b* installed at a position where the X-ray detector 27*b* faces the X-ray generator 27*a*.

11 Claims, 12 Drawing Sheets

(51) Int. Cl.
*A61B 6/00* (2006.01)
*A61B 6/04* (2006.01)

(52) U.S. Cl.
CPC .......... *A61B 6/4007* (2013.01); *A61B 6/4014* (2013.01); *A61B 6/4266* (2013.01); *A61B 6/4435* (2013.01); *A61B 6/4452* (2013.01); *A61B 6/587* (2013.01); *A61N 5/10* (2013.01); *A61N 5/1078* (2013.01); *A61B 6/4233* (2013.01); *A61B 6/4476* (2013.01); *A61N 5/1081* (2013.01); *A61N 2005/1061* (2013.01); *A61N 2005/1087* (2013.01)

(58) Field of Classification Search
USPC ................ 250/396 R, 397, 492.1, 492.3
See application file for complete search history.

(56) References Cited

U.S. PATENT DOCUMENTS

| | | | |
|---|---|---|---|
| 2008/0315111 | A1 | 12/2008 | Sommer |
| 2011/0024645 | A1 | 2/2011 | Hagino et al. |
| 2017/0001041 | A1 | 1/2017 | Yamashita et al. |
| 2017/0340903 | A1 | 11/2017 | Ie |
| 2018/0289981 | A1* | 10/2018 | Nagamoto ........... A61B 6/4007 |

FOREIGN PATENT DOCUMENTS

| | | |
|---|---|---|
| JP | 3519248 B2 | 4/2004 |
| JP | 3927348 B2 | 6/2007 |
| JP | 4130680 B2 | 8/2008 |
| JP | 2012-513852 A | 6/2012 |
| JP | 2017-12374 A | 1/2017 |
| WO | WO 2006/076545 A2 | 7/2006 |
| WO | WO 2010/076270 A1 | 7/2010 |

* cited by examiner

FIG. 11A
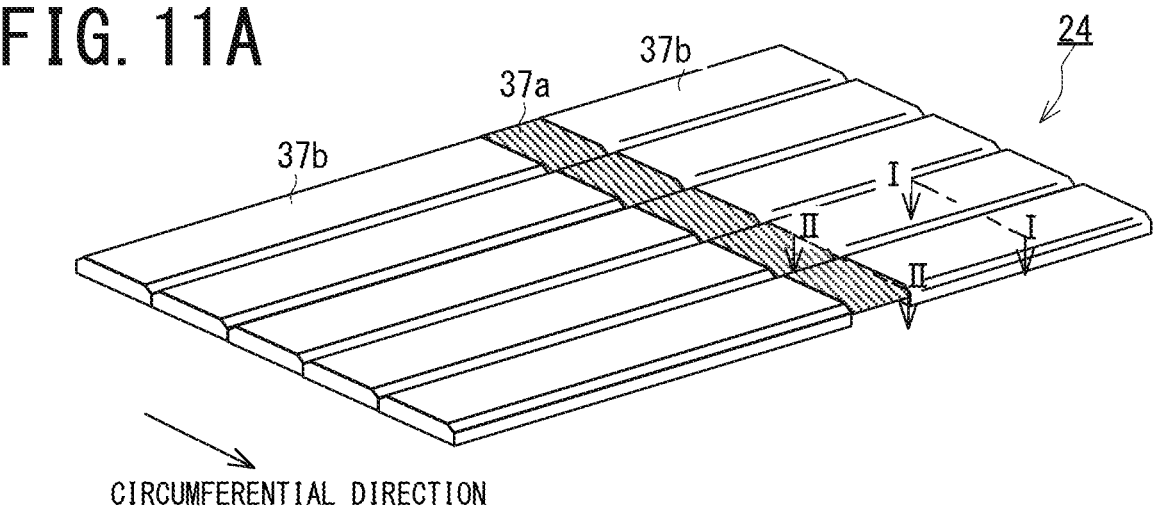
CIRCUMFERENTIAL DIRECTION
FIG. 11B I-I CROSS-SECTION
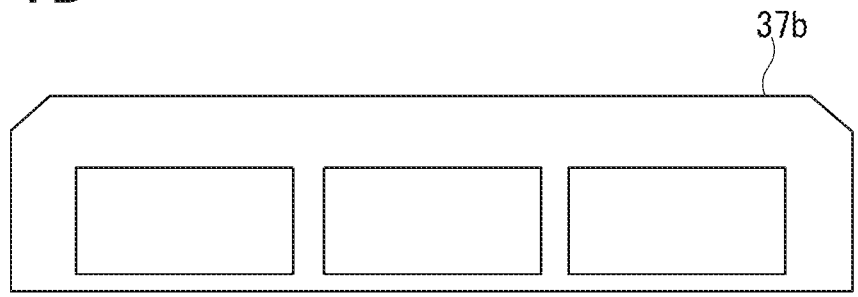
FIG. 11C II-II CROSS-SECTION
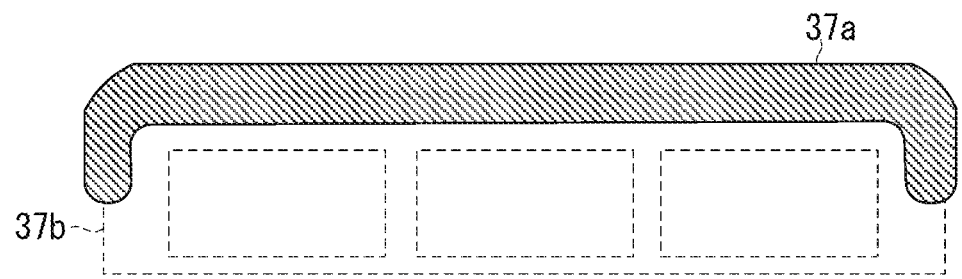

PARTICLE BEAM THERAPY APPARATUS

CROSS-REFERENCE TO RELATED APPLICATIONS

The present application is a continuation of U.S. application Ser. No. 15/763,634, filed Mar. 27, 2018, which is based on PCT/JP2016/078762 filed Sep. 29, 2016, which claims priority to JP 2015-192811, filed Sep. 30, 2015, the entire contents of each of which are incorporated herein by reference.

FIELD

Embodiments of the present invention relate to a particle beam therapy apparatus (i.e., particle beam therapy device) equipped with a rotating gantry.

BACKGROUND

In cancer treatment in recent years, a particle beam therapy method is widely used. In the particle beam therapy method, a cancer lesion area is irradiated with a particle beam that is generated by accelerating charged particles such as protons and carbon ions to high energy.

In the particle beam therapy method, in order to irradiate a cancer lesion area with a particle beam without irradiating important organs, it is required to perform irradiation changing the irradiation angle of the beam variously. Thus, for instance, a particle beam irradiator is fixed to a cylindrical rotating gantry to rotate together, thereby is changed its irradiation angle.

The inner space of the rotating gantry serving as a treatment room is provided with a movable floor that maintains a flat horizontal floor surface regardless of the rotation of the rotating gantry.

By using the movable floor, a technician accesses a patient before and after treatment and the patient comes down from the treatment table in case of emergency.

In order not to hinder the displacement of a tip portion of a particle beam irradiator which is fixed to the treatment room to protrude its tip portion into the treatment room, the movable floor slides in accordance with the displacement of the tip portion.

Before or during the irradiation of the particle beam, X-ray imaging is performed so that the position and shape of the lesion area are accurately analyzed.

Thus, an X-ray generator for radiating X-rays toward the patient and an X-ray detector for detecting X-rays transmitted through the patient (hereinafter, both are referred to as "X-ray imaging devices") are arranged in the treatment space.

Since a particle beam therapy apparatus is equipped with some devices that change their relative positions as described above, it is necessary to consider the changes of the relative arrangements of the X-ray imaging devices.

For instance, there is a known method of connecting arms with the X-ray imaging devices and storing the arms together with the X-ray imaging devices at a place that the arms and the X-ray imaging devices do not collide with any other device in the treatment room.

In this case, the arms being controlled so as not to hinder the replacements of other devices, the X-ray generator is placed in the vicinity of the lesion area only at the time of X-ray irradiation, and after the completion of imaging, the X-ray generators are retracted.

However, the above-described technique has a problem that the arms and their control mechanisms complicate the particle beam therapy apparatus and the treatment time is prolonged by the arrangement time and retraction time of the X-ray imaging devices.

Nevertheless, X-ray images acquired by X-ray imaging are required to be clear to the extent that the position of the lesion area can be accurately specified.

PRIOR ART DOCUMENT

Patent Document

[Patent Document 1] Japanese Patent No. 3519248
[Patent Document 2] Japanese Patent No. 3927348
[Patent Document 3] Japanese Patent No. 4130680

SUMMARY OF THE INVENTION

Problem to be Solved by the Invention

An object of the present invention is to provide a particle beam therapy apparatus that can acquire a high-quality X-ray image with a simple structure and shorten treatment time.

Means for Solving Problem

In one embodiment, a particle beam therapy apparatus includes: a particle beam irradiator configured to output a particle beam; a supporting structure configured to be movable and support the particle beam irradiator; a plurality of movable plates disposed on a displacement trajectory of the particle beam irradiator, forming a substantially horizontal enveloping surface below a table for placing an irradiation object, and including a first floor member and a second floor member in at least one of the plurality of movable plates, the second floor member having larger transmittance of X-ray than the first floor member; an X-ray generator provided in a non-collision area where the X-ray generator does not collide with any of the particle beam irradiator, the supporting structure, and the plurality of movable plates; and an X-ray detector installed at a position where the X-ray detector faces the X-ray generator and detects X-rays transmitted through the first floor member.

BRIEF DESCRIPTION OF DRAWINGS

FIG. 11A is a perspective view of movable plates included in the particle beam therapy apparatus according to the fourth embodiment.

FIG. 11B is a cross-sectional view taken along the line I-I in FIG. 11A.

FIG. 11C is a cross-sectional view taken along line II-II in FIG. 11A.

DESCRIPTION OF EMBODIMENTS

Hereinafter, embodiments of the present invention will be described with reference to the accompanying drawings.

Figure 1:
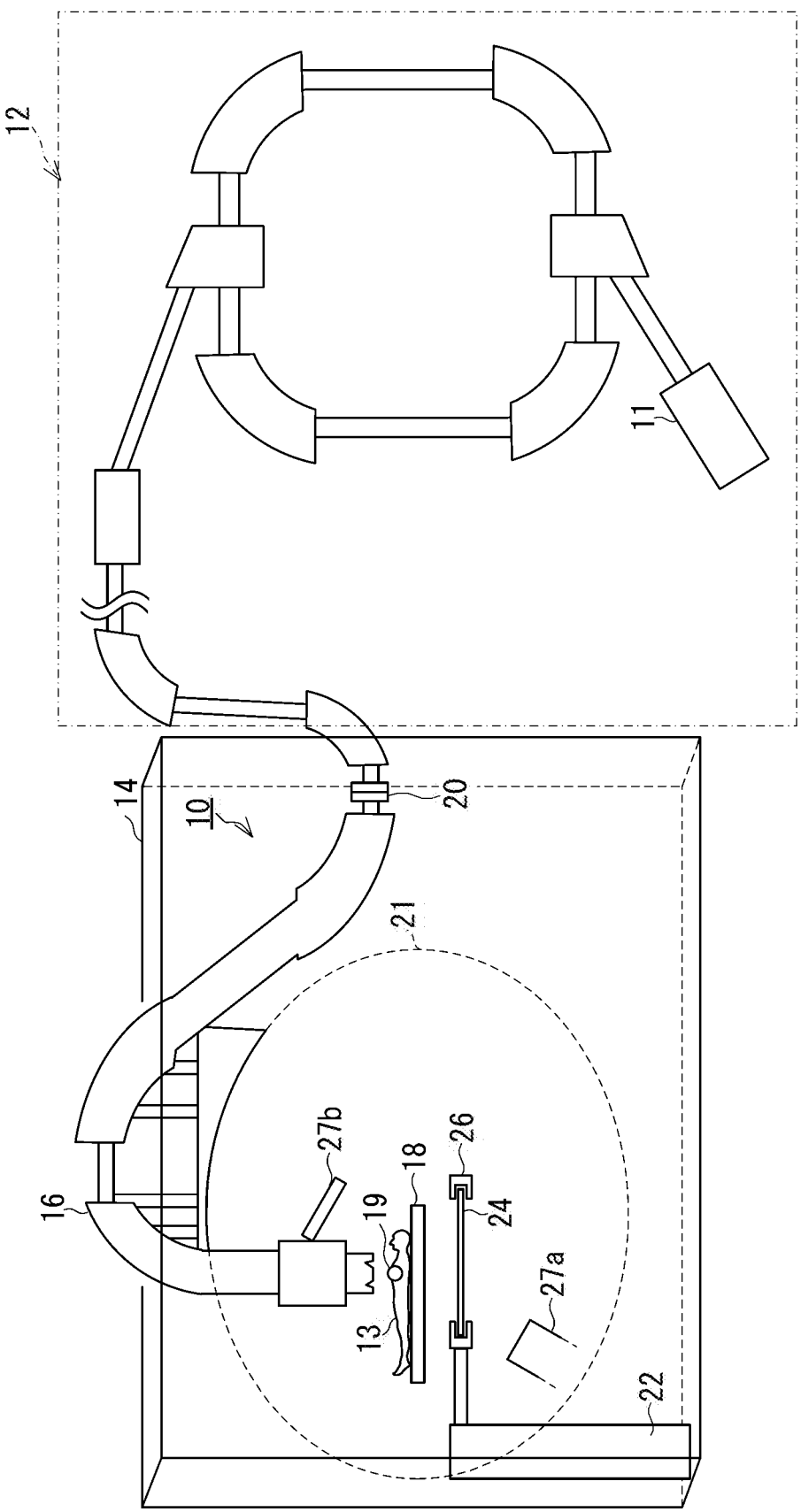
FIG. 1 is a schematic configuration diagram of a particle beam therapy apparatus according to one embodiment.

FIG. 1 is a schematic configuration diagram of the particle beam therapy apparatus 10 (hereinafter simply referred to as the treatment apparatus 10) according to one embodiment.

Charged particles such as protons or carbon ions emitted from an ion source 11 form a particle beam B accelerated by a particle beam accelerator 12.

The particle beam B is guided with magnetic field to a treatment building 14 where a patient 13 as an irradiation object is present.

Further, the particle beam B is guided to a particle beam irradiator 16 that is connected to the accelerator 12 via a rotary joint 20, and then is outputted toward the lesion area 19 of the patient 13 fixed to the table 18 from the tip portion of the particle beam irradiator 16.

In order to maintain the posture of the particle beam irradiator 16 that variously changes its irradiation angle, the particle beam irradiator 16 is supported by a rotating gantry 21.

The rotating gantry 21 is a rotating structure provided as a supporting structure for supporting the particle beam irradiator 16.

The particle beam irradiator 16 can take various postures subjecting the displacement, such as rotation, of the rotating gantry 21 with respect to the treatment building 14.

As to the table 18 placed on a treatment mount that is fixed to a base 22 built in the treatment building 14, the table 18 can also change the posture within such a range that excessive load is not exerted on the patient 13.

Since a person involved, such as the patient 13 or a technician 38 (FIG. 28), accesses the periphery of the table 18, a floor surface configured to keep horizontality regardless of displacement of the rotating gantry 21 is disposed below the table 18.

When the portion of the floor surface disposed in the passing trajectory of the particle beam irradiator 16 is not displaced, the displacement of the particle beam irradiator 16 is hindered.

Figure 5:
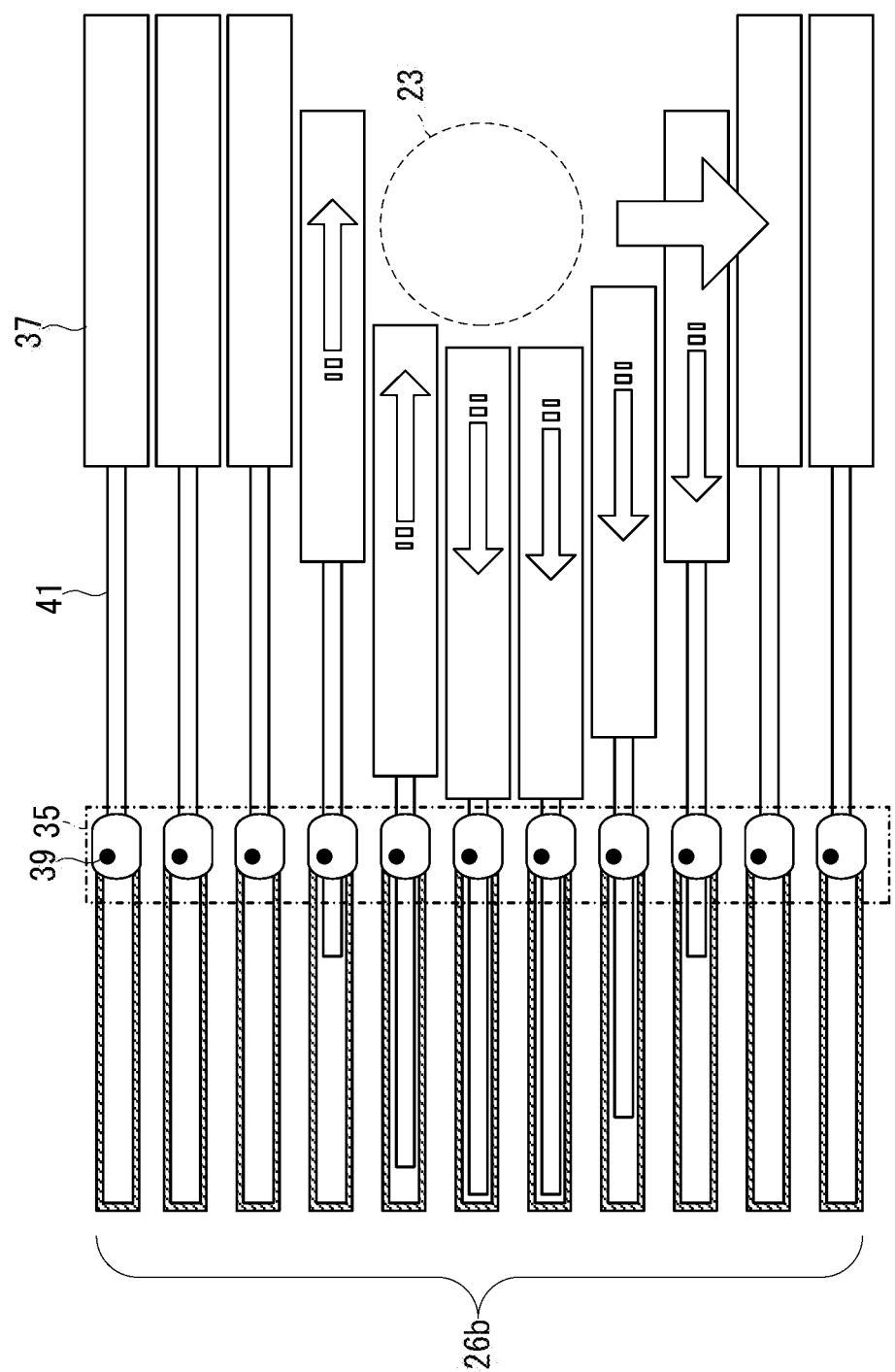
FIG. 5 is a top view illustrating a movable floor of lateral sliding type as a modification.

For this reason, at least the floor surface in the passing trajectory needs to be configured to be a movable floor 24 that is retracted from an occupied area 23 (FIG. 5) to be occupied by the particle beam irradiator 16 in accordance with passage of the particle beam irradiator 16.

The movable floor 24 slides by being fixed to the base 22 directly or via the floor surface or by being slidably engaged with support guides 26a disposed inside the rotating gantry 21.

Details of the movable floor 24 will be described below.

Further, the treatment apparatus 10 is equipped with X-ray generators 27a (27) and X-ray detectors 27b (27). Each X-ray generator 27a is installed so as to face the patient 13 and emits X-rays, and each X-ray detector 27b (i.e., Flat Panel Detector: FPD) detects X-rays transmitted through the patient 13.

Hereinafter, these X-ray generators 27a and the FPDs 27b are arbitrarily and collectively referred to as X-ray imaging devices 27.

In order to shot the periphery of the lesion area 19 clearly by using X-rays, the X-ray imaging devices 27 need to be placed on or near the passage trajectory of the particle beam irradiator 16 at least at the time of X-ray imaging.

For this reason, in the treatment apparatus 10 according to the present embodiment, the respective X-ray imaging devices 27 are fixed and installed at such positions in a non-collision area 31 that each X-ray generator 27a faces the corresponding FPD 27b with the movable floor 24 interposed between both.

The non-collision area 31 is an area where the X-ray imaging devices 27 do not collide with any of the particle beam irradiator 16, the rotating gantry 21, and the movable floor 24 without using an electronic position control mechanism.

Hereinafter, embodiments of the treatment apparatus 10 shown in FIG. 2 to FIG. 12 will be described including the description of the non-collision area 31.

First Embodiment

Figure 2:
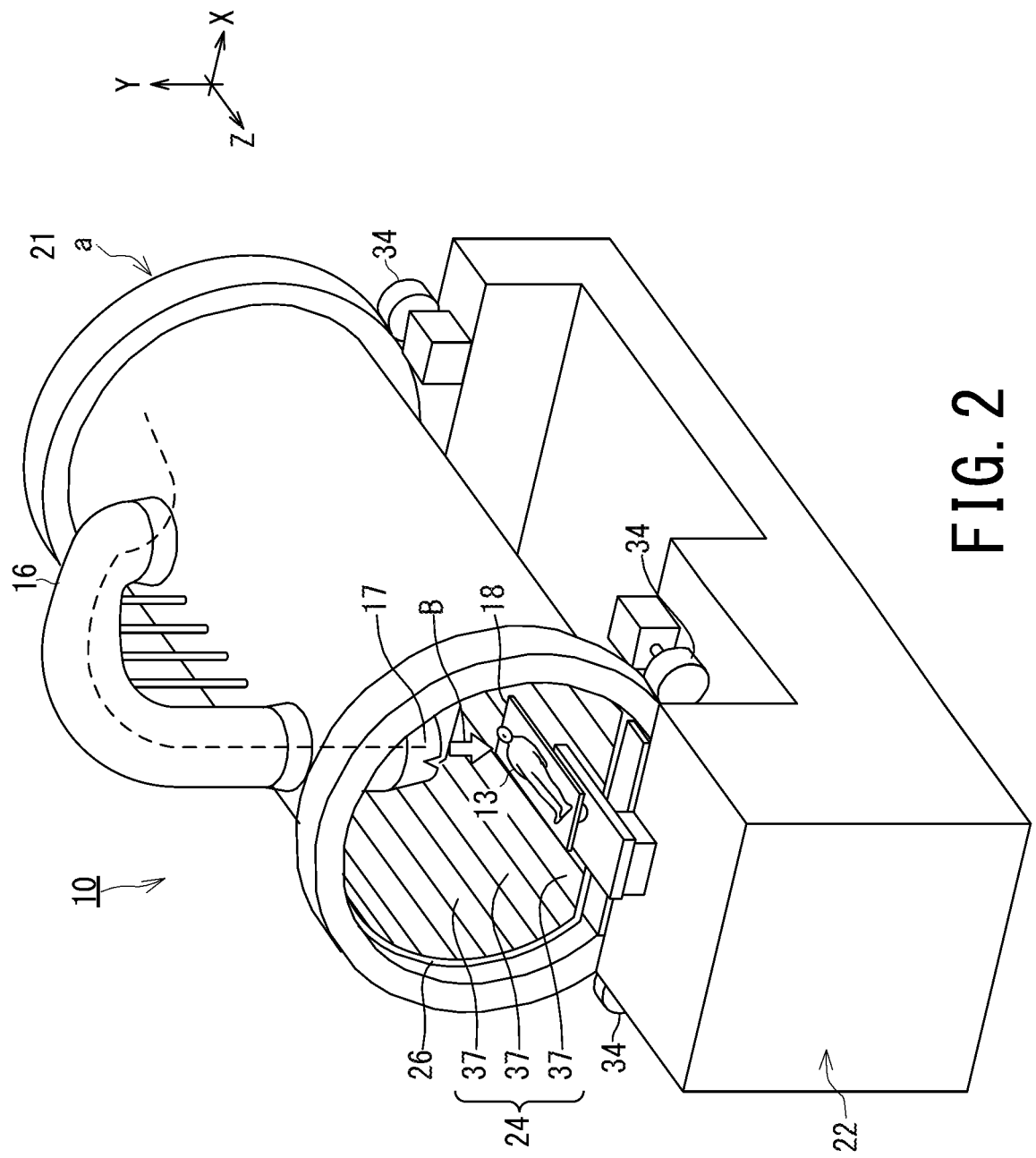
FIG. 2 is a diagram illustrating the particle beam therapy apparatus equipped with a rotating gantry of full rotation type according to the first embodiment.

FIG. 2 is a diagram illustrating the treatment apparatus 10 according to the first embodiment equipped with a rotating gantry 21a of full rotation type.

Since the particle beam irradiator 16 is provided with a large number of structures (not shown) such as a vacuum duct, a beam deflection electromagnet, an irradiation field forming electromagnet, various monitors, and a gantry, the particle beam irradiator 16 is considerably heavy.

Thus, in many cases, a cylindrical rotating gantry 21a (21) of full rotation type as shown in FIG. 2 is used in order to stably support and displace the heavy particle beam irradiator 16.

Such a rotating gantry 21a is placed on, e.g., rotation drivers 34 that are installed on the base 22, and rotates around the central axis (i.e., Z axis) of the cylinder by the rotation of the rotation driver 34.

The particle beam irradiator 16 is fixed in such a manner that the tip portion of the particle beam irradiator 16 protrudes toward treatment space 36.

By forming the base 22 into a concave shape around the trunk portion of the rotating gantry 21a, the rotating gantry 21a can rotate 360 degrees around the central axis without causing the outer protrusion of the particle beam irradiator 16 to collide with the base 22.

Figure 3A:
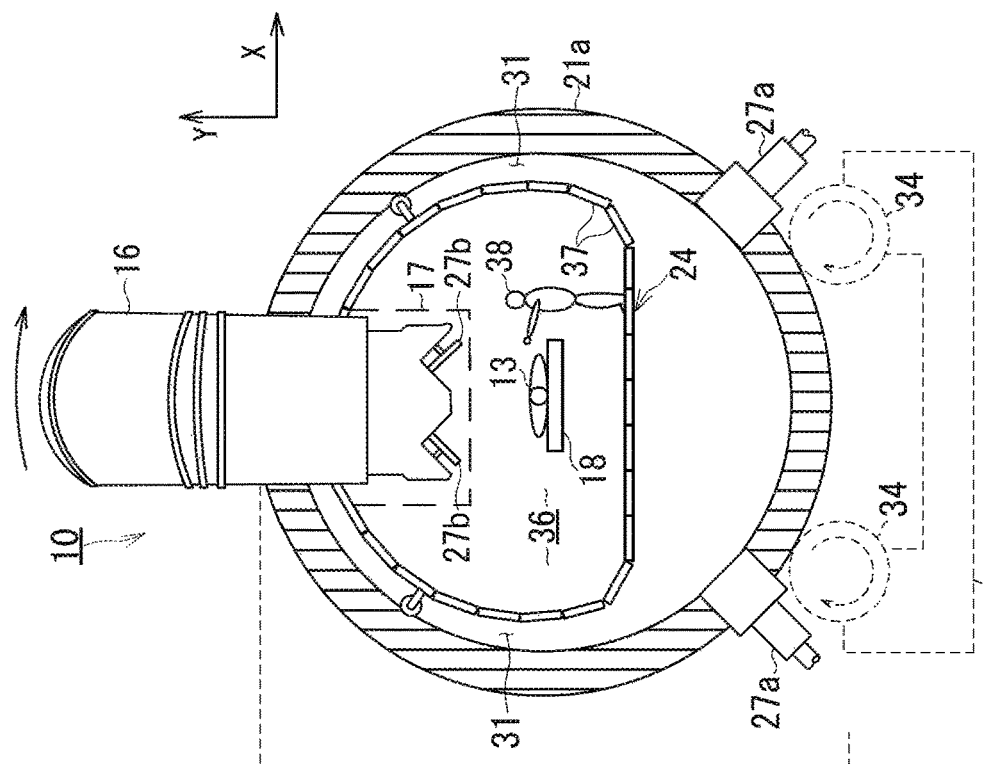
FIG. 3A is a cross-sectional view of the particle beam therapy apparatus according to the first embodiment, taken along the central axis of the rotating gantry.

FIG. 3A is a cross-sectional view of the treatment apparatus 10, a cross-sectional view taken along the central axis of the rotating gantry 21*a* shown in FIG. 2.

Figure 3B:
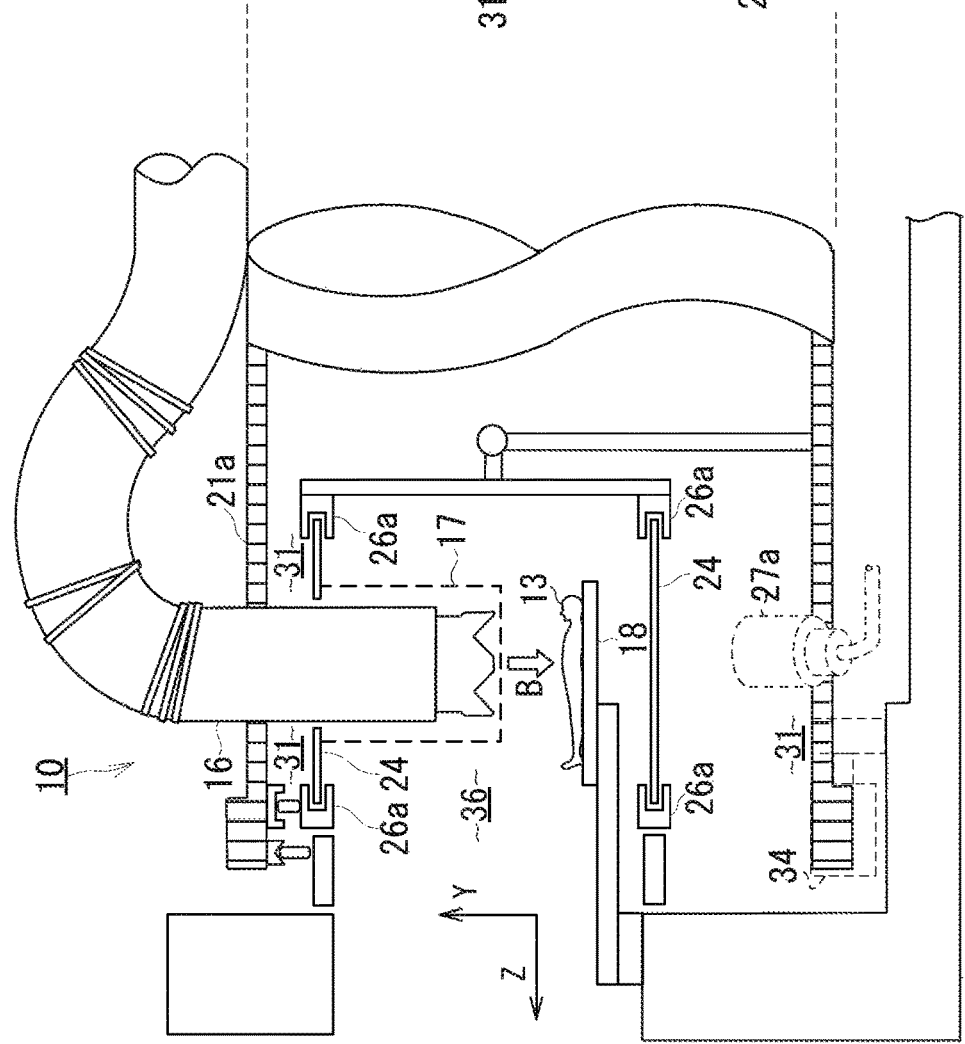
FIG. 3B is a cross-sectional view of the particle beam therapy apparatus according to the first embodiment, taken along the direction perpendicular to the central axis of the rotating gantry.

FIG. 3B is a cross-sectional view of the treatment apparatus 10, taken along the direction perpendicular to the central axis.

Figure 4:
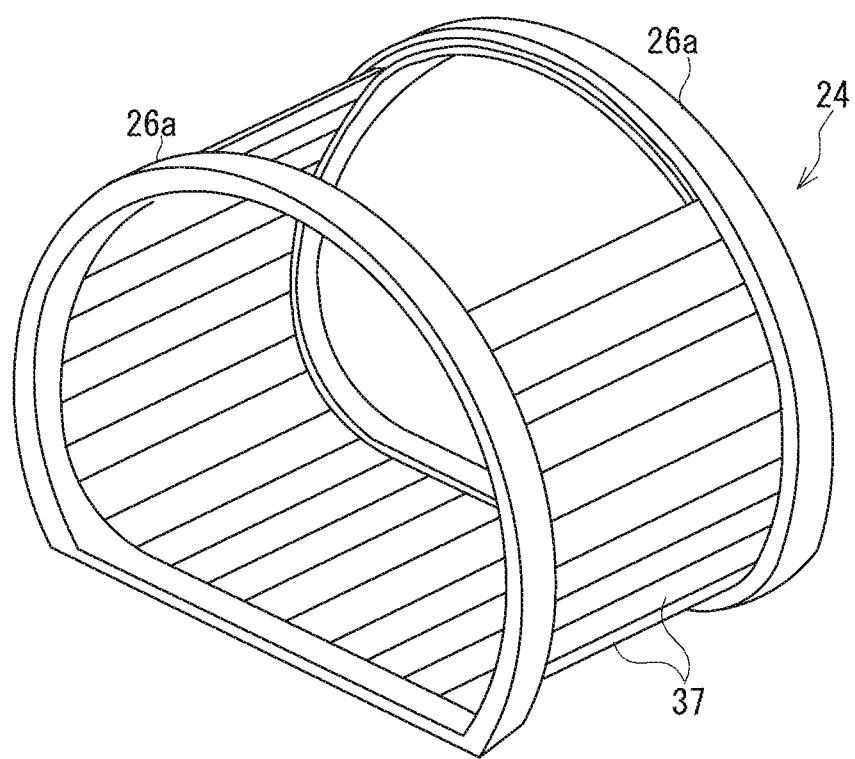
FIG. 4 is a perspective view illustrating a movable floor provided on a support guide.

FIG. 4 is a perspective view illustrating the movable floor 24 provided on the support guides 26*a*.

(Arrangement of Movable Floor 24)

As shown in FIG. 3A and FIG. 4, the movable floor 24 is formed by, e.g., juxtaposing a group of longitudinal movable plates 37 along the support guides 26*a*.

Each support guide 26*a* is composed of, e.g., a horizontal portion that is horizontal below the table 18 and a curved portion that is curved along the inner peripheral surface of the rotating gantry 21*a* and is connected to both ends of the horizontal portion.

Two support guides 26 formed into the above-described shape are arranged so as to face each other as a pair and are engaged with both end portions in the longitudinal direction of each movable plate 37.

The movable plates 37 are slidable along the support guides 26*a* by being engaged with the support guides 26*a* via, for example, non-illustrated motor-rotating rollers.

The group of the movable plates 37 below the table 18 forms a horizontal enveloping surface so as to serve as the movable floor 24.

In the present description, the term "slide" means that the members contacted to each other move relative to each other keeping the contact.

For instance, "slide" includes relative movement with rollers or gears or sliding on a contacted smooth surface.

The particle beam irradiator 16 is fixed in such a manner that the tip portion of the particle beam irradiator 16 is inserted into a position sandwiched between the pair of the support guides 26*a*.

That is, a part of the entire circumference of each support guides 26*a* is configured as a region where the movable plate 37 does not exist for inserting the tip portion of the particle beam irradiator 16*a*.

When the particle beam irradiator 16 is rotated by the rotation of the rotating gantry 21*a*, the movable plates 37 are pushed by the particle beam irradiator 16 and slide along the circumferential direction of the particle beam irradiator 16.

In other words, the movable plates 37 are slid in the advancing direction of the particle beam irradiator 16 and are retracted from the occupied area 23 (FIG. 5) by the particle beam irradiator 16.

As shown in FIG. 5*a* illustrating the top view of a movable floor 24 of lateral sliding type as a modification of movable floor 24, the retracting direction of the movable plate 37 may be perpendicular to the circumferential direction of the particle beam irradiator 16.

In the case of the movable floor 24 of lateral sliding type, for instance, plural linear support guides 26*b* are provided along the central axis of the rotating gantry 21*a*.

Further, the sliding driver 35 detects the circumferential angle of the particle beam irradiator 16 around the central axis of the rotating gantry by using a passage sensor 39, and then slides the shaft 41 connected to the movable plates 37 along the support guides 26*b*.

The "circumferential angle" is defined as a rotation angle around the central axis of the rotating gantry 21 from the position as zero degree at which the particle beam irradiator 16 stops vertically upward. This definition will be also applied to the following description.

The movable floor 24 is pulled by the shaft 41 so as to be retracted from the occupied area 23 of the particle beam irradiator 16.

(Arrangement of X-Ray Imaging Devices 27)

When the rotating gantry 21 is the rotating gantry 21*a* of full rotation type, the X-ray generators 27*a* are fixed to, e.g., the trunk of the rotating gantry 21*a*.

By fixing the X-ray generators 27*a* to the rotating gantry 21*a*, the X-ray generators 27*a* also rotate together with the rotating gantry 21*a*, and thus the X-ray generators 27*a* do not collide with the particle beam irradiator 16.

In other words, the non-collision area 31 is (a) the inside of the wall of the trunk of the rotating gantry 21*a* and (b) a gap between the curved surface of the movable floor 24 and the inner peripheral surface of the trunk of rotating gantry 21*a*.

That is, this area is a non-collision area 31 where the X-ray generators 27*a* do not collide with, for example, the particle beam irradiator 16 without using an electronic position control mechanism.

In this case, when the FPD 27*b* is provided at the tip portion of the particle beam irradiator 16, the relative angle between each FPD 27*b* and the corresponding X-ray generator 27*a* does not change and the installation angle of the X-ray detection plane can be fixed.

The FPDs 27*b* installed in the particle beam irradiator 16 never collide with the particle beam irradiator 16 and never hinder displacement of the particle beam irradiator 16.

In other words, when the FPDs 27*b* are fixed to the particle beam irradiator 16, the vicinity of the tip portion of the particle beam irradiator 16 is the non-collision area 31 within a range in which the FPDs 27*b* do not hinder the displacement of the particle beam irradiator 16.

On the protruding portion of the particle beam irradiator 16 protruding toward the inside of the rotating gantry 21*a*, a cover 17 for covering the protruding portion is provided.

Even when each FPD 27*b* is provided on the inner surface or the outer surface of the cover 17, each FPD 27*b* does not hinder the displacement of the particle beam irradiator 16 and the like.

Thus, even when the respective FPD s27*b* are provided on the inner surface and the outer surface of the cover 17, the FPDs 27*b* are equivalent to being provided in the non-collision area 31.

Even when the installation angle can be fixed, the FPDs 27*b* may be housed in the particle beam irradiator 16 or the cover 17.

The fixed portion of the particle beam irradiator 16 on the inner circumferential surface of the rotating gantry 21*a* may protrude to be exposed to the treatment space 36.

In this case, the FPDs 27*b* may be installed in the exposed portion (not shown), and the vicinity of the exposed portion is also the non-collision area 31.

Preferably, two pairs of the X-ray imaging devices 27 are installed at an angle of ±45 degrees from the beam irradiation axis.

By acquiring respective X-ray images from two directions, it is possible to grasp the three-dimensional position of the lesion area 19.

In addition, installing the respective two pairs of the X-ray imaging devices 27 in the horizontal direction and the vertical direction makes it possible to use an image processing method common to the conventional fixed irradiation chamber.

Further, it is possible to install X-ray generators 27*a* in the treatment space 36 such as in the vicinity of the tip portion of the particle beam irradiator 16 while the FPDs 27*b* is installed in the rotating gantry 21*a* while the X-ray generators 27*a*, namely reversing the positions of the X-ray generators 27*a* and the FPDs 27*b*.

Although it is not specifically shown, the respective positions of the X-ray generators 27*a* and the FPDs 27*b* can be exchanged in all the following embodiments.

(Configuration of Moving Plates 37)

As described above, when the X-ray generators 27*a* are installed in the rotating gantry 21*a* and the FPDs 27*b* are installed in, for example, the particle beam irradiator 16, the movable floor 24 is disposed between the X-ray generators 27*a* and the FPDs 27*b*.

In other words, the X-rays emitted from the X-ray generators 27*a*, being shielded by the movable floor 24, do not reach the FPDs 27*b* on the side opposite to the corresponding X-ray generator 27*a* with respect to the movable floor 24.

Figure 6B:
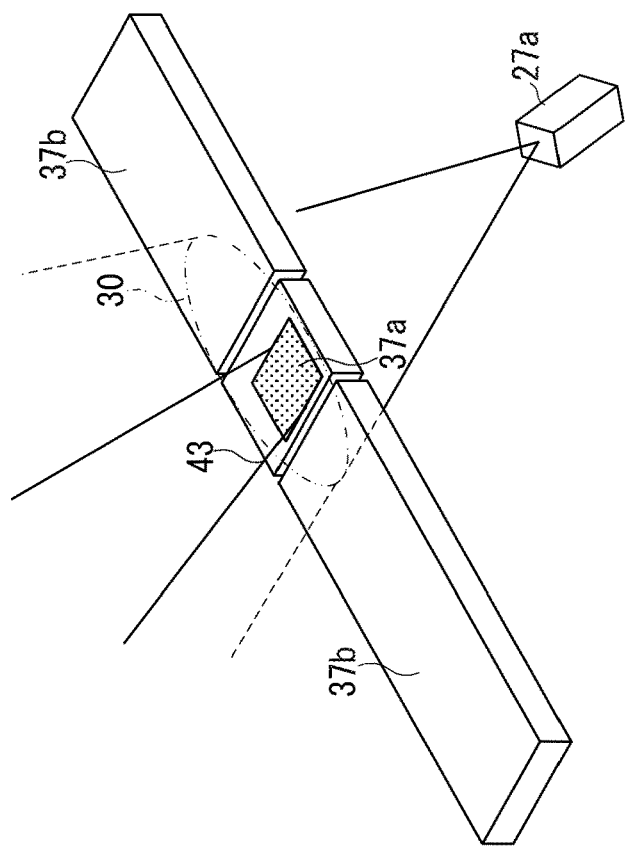
FIG. 6B is a schematic diagram illustrating a case where X-rays are radiated onto the movable plate shown in FIG. 6A.
Figure 6A:
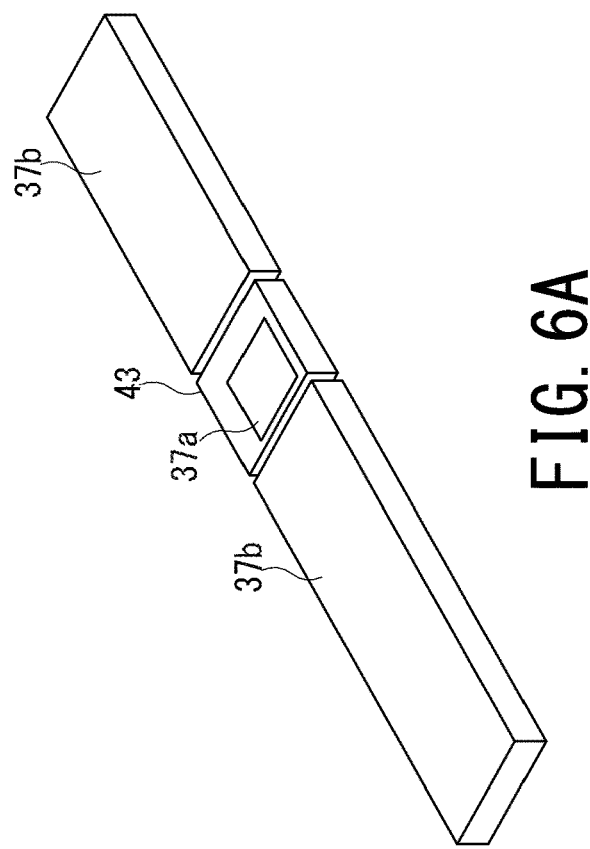
FIG. 6A is a perspective view illustrating each movable plate of the particle beam therapy system according to the first embodiment.

For this reason, as illustrated by the movable plate 37 in FIG. 6A, the movable plate 37 is composed of a first floor member 37*a* and a second floor member 37*b* (37) that is different in X-ray transmittance from the first floor member 37*a*.

The second floor member 37*b* as the base material of the movable plate 37 is, e.g., an aluminum alloy (e.g., JISA5052) having a width of about 400 mm and a length of about 2000 mm, and has sufficient strength as a floor surface for the patient 13 to get on and off.

The first floor member 37*a* (37) is made of a material that is higher in X-ray transmittance than the second floor member 37*b*.

In other words, the ratio η of the transmittance of the first floor member 37*a* to the second floor member 37*b* is selected so as to become larger than 1.

For instance, carbon-fiber-reinforced plastic (CFRP) has high strength against X-ray transmittance and is suitable as a material for the first floor member 37*a*.

It is known that the X-ray transmittance of CFRP is about 5 times larger than that of aluminum of the same thickness.

The material of the first floor member 37*a* ma be the same as that of the second floor member 37*b*.

Even when the first floor member 37*a* and the second floor member 37*b* are made of the same material, the X-ray transmittance of the first floor member 37*a* can be increased by reducing the thickness of the first floor member 37*a*.

(Installation Position of First Floor Member 37*a*)

FIG. 6B is a schematic diagram of the movable plate 37 when the movable plate 37 shown in FIG. 6A is irradiated with X-rays.

The irradiation range of X-rays outputted from the X-ray generator 27*a* has a certain spread.

It is sufficient that the patient 13 is irradiated with, for example, the minimum amount of X-rays by which the position of the lesion area 19 or a marker embedded around the lesion area 19 can be specified.

In other words, a part of X-rays emitted from the X-ray generator 27*a* reaches the patient 13, and then is detected by the FPD 27*b*.

For this reason, as shown in FIG. 6B, the first floor member 37*a* is provided in such an area on the movable plate 37 that the intersection plane 30 is included, the intersection plane 30 being the area where the movable plate 37 cuts the irradiation cone area.

As shown in FIG. 6B, for instance, a frame 43 is provided on the first floor member 37*a*, and the first floor member 37*a* is coupled to the second floor member 37*b* via the frame 43.

It is assumed that the frame 43 is included in the second floor member 37*b* except for special cases such as a case where a material for transmitting X-rays is selected.

The term "coupled" as used herein also includes a case where the second floor member 37*b* is punched and the first floor member 37*a* is interdigitated with the punched portion.

When a screw is used for coupling the first floor member 37*a*, the first floor member 37*a* can be easily removed, and the X-ray generators 27*a* can be confirmed without detaching the entire movable plate 37.

The method for joining the first floor member 37*a* is not limited to a particular one, and welding or bonding with the use of an adhesive agent other than screw bonding may be used.

In addition, by setting the size of the punched portion one size larger than that of each X-ray generator 27*a*, each X-ray generator 27*a* can be easily taken in and out through this punched portion.

In many cases, the movable plate 37 provided with the first floor member 37*a* has a lower strength than the movable plate 37 that is not provided with the first floor member 37*a*.

For this reason, it is desirable to provide the first floor member 37*a* only on the minimized number of specific movable plates 37.

For instance, two pairs of the X-ray imaging devices 27 are often fixed at an angle of ±45 degrees from the irradiation axis of the particle beam irradiator 16 for the above-described reason.

Thus, as for the movable floor 24 provided with the first floor members 37*a*, the movable floor 24 would be provided on the region at an angle of ±45° from the irradiation axis and is also provided on several movable plates 37 in the vicinity of this region.

As described above, according to the treatment apparatus 10 of the first embodiment, a high-quality X-ray image can be acquired with a simple configuration.

In addition, since it is not necessary to retract the X-ray imaging devices 27, treatment time can be shortened.

[Second Embodiment] (Rotating Gantry 21*b* of Partial Rotation Type)

Figure 7:
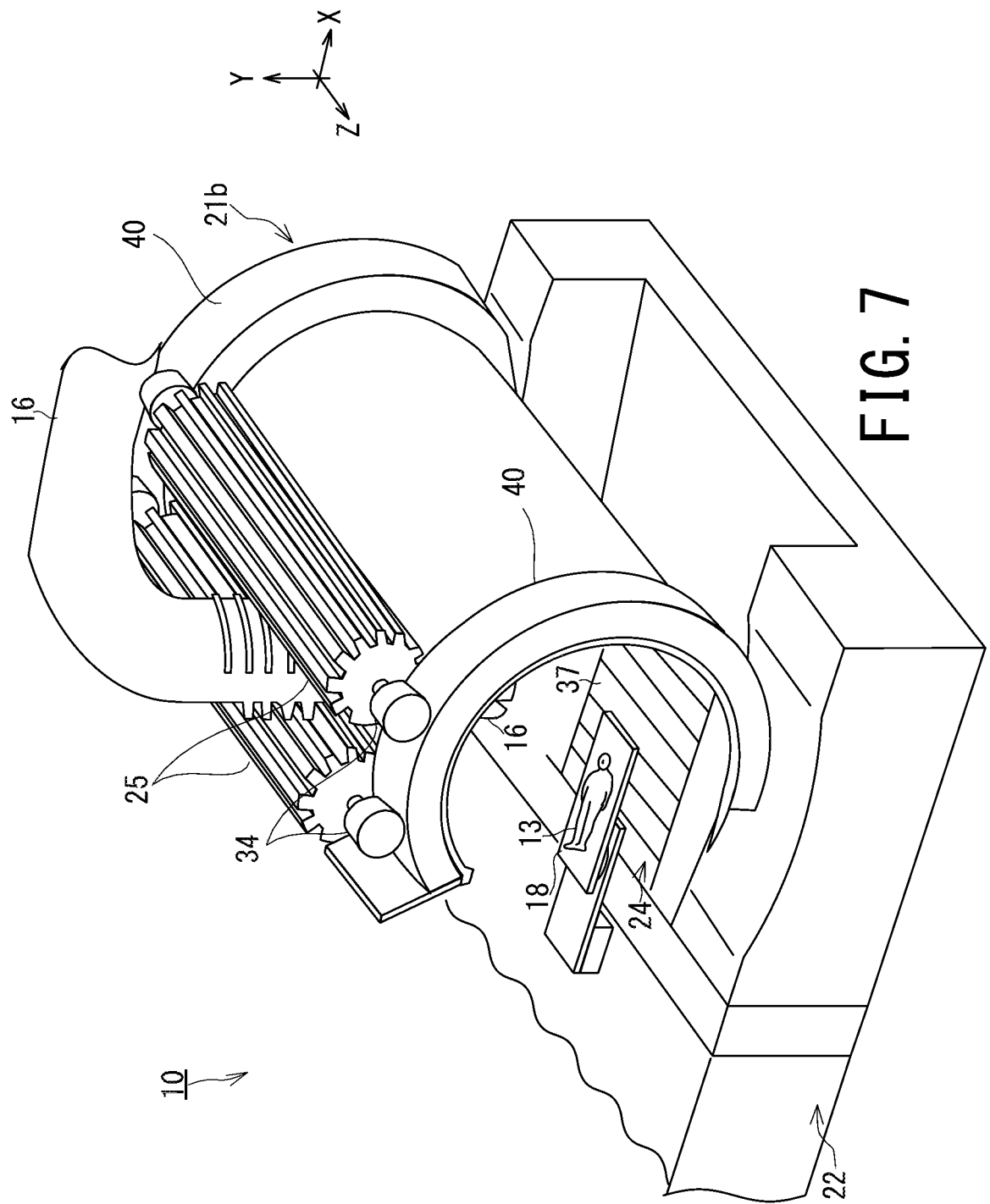
FIG. 7 is a schematic configuration diagram of the particle beam therapy system according to the second embodiment.

FIG. 7 is a schematic configuration diagram of the treatment apparatus 10 according to the second embodiment.

In recent years, as shown in FIG. 7, there is known a rotating gantry 21*b* (21) of partial rotation type with the use of, for example, rail tracks 40 or a part of a cylinder.

In FIG. 7, various accompanying devices such as balance weights that are connected to the particle beam irradiator 16 and balance the weight with the particle beam irradiator 16 are omitted.

In the rotating gantry 21*b* shown in FIG. 7, two rail tracks 40 in a curved shape and in an angle range smaller than 360 degrees are provided.

Two rotation auxiliary bodies 25 are engaged with these two rail tracks 40.

The particle beam irradiator 16 is supported by the rotation auxiliary bodies 25 and rotates at an angle smaller than 360 degrees around the patient 13 fixed to the table 18.

In the case of using the rotating gantry 21*b*, by limiting the displacement angle of the particle beam irradiator 16 and horizontally rotating the table 18, it is possible to radiate the particle beam B from an arbitrary angle in the same manner as the rotating gantry 21*a* of full rotation type.

By limiting the displacement angle, it is possible to secure a large non-collision area 31 in the vicinity of the table 18.

In the second embodiment, a description will be given of the case where the treatment apparatus 10 is applied to the rotation gantry 21b of partial rotation type.

Figure 8:
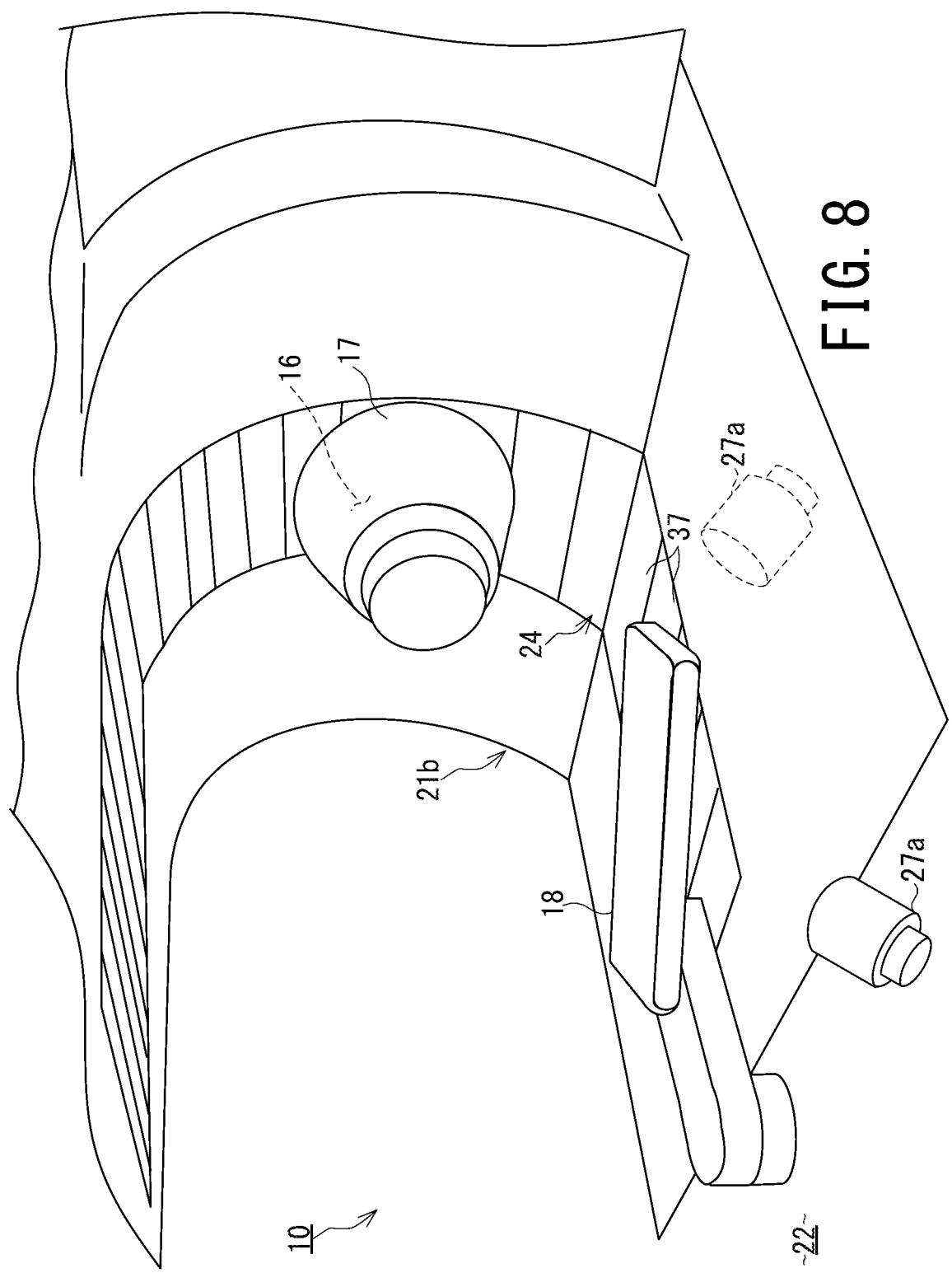
FIG. 8 is a schematic configuration diagram of treatment space of a rotating gantry of partial rotation type.

FIG. 8 is a schematic configuration diagram of the treatment space of the rotation gantry 21b.

As shown in FIG. 8, the treatment apparatus 10 of the second embodiment differs from the first embodiment in that it is possible to enter and leave from the position of the trunk of the rotating gantry 21 in a direction perpendicular to the center axis.

Thus, the table 18 is placed close to the base 22 during treatment.

Accordingly, for instance, one of the two X-ray generators 27a is fixed to a portion that is not displaced regardless of the rotation of the rotating gantry 21b, such as the base 22.

When X-rays are emitted from the X-ray generator 27a fixed to the base 22, the X-rays emitted to the FPD 27b are radiated onto the patient 13 without being shielded by the movable floor 24.

Thus, as to the X-ray imaging devices 27 including the X-ray generator 27a fixed to the base 22, contrivance like the first embodiment is unnecessary for the movable plates 37.

However, as described above, in order to acquire the three-dimensional position coordinates of the lesion area 19, it is necessary for the two X-ray generators 27a to be installed with an angle of, e.g., 90 degrees difference.

Thus, even with the rotation gantry 21b of partial rotation type, the remaining one X-ray generator 27a is arranged at a position so as to face the corresponding FPD 27b with the movable floor 24 interposed between both in a manner similar to the first embodiment.

Hence, the first floor member 37a is provided on the movable plate 37 in a manner similar to the first embodiment so that X-ray imaging can be performed also in the remaining pair of the X-ray imaging devices 27.

Although it is not shown, the PDF to be paired with the X-ray generator 27a installed on the base 22 is provided at, e.g., the tip of the particle beam irradiator 16.

Further, the PDF to be paired with the X-ray generator 27a installed in the rotating gantry 21b is provided on, e.g., the base 22.

As described above, according to the second embodiment, even when the rotating gantry 21b is a partial rotating type, the same effect as the first embodiment can be obtained.

Note that the particle beam therapy apparatus of the second embodiment has the same structure as that of the first embodiment except that the rotating gantry 21 is the rotating gantry 21b of partial rotating type, and duplicate description is omitted.

The same reference signs are assigned to the same components in terms of configuration or function as the first embodiment in each figure, and duplicate description is omitted.

As described above, the same effects as in the first embodiment can be obtained also in the treatment apparatus 10 according to the second embodiment.

[Third Embodiment] (Correction of Relative Peripheral Angle of First Floor Member 37a and Particle Beam Irradiator 16)

FIG. 9A and FIG. 9B are schematic cross-sectional views illustrating the treatment apparatus 10 according to the third embodiment.

FIG. 9A is a cross-sectional view of the treatment apparatus 10 equipped with the rotating gantry 21a of full rotation type shown in FIG. 2, taken along the central axis of the rotating gantry 21a in a manner similar to FIG. 3A.

In addition, FIG. 9B is a cross-sectional view of the treatment apparatus 10 in the direction perpendicular to the central axis, similarly to FIG. 3B.

As shown in FIG. 9A and FIG. 9B, in addition to the configuration of the first embodiment, the treatment apparatus 10 according to the third embodiment further includes a sensor 44 for detecting the position of the first floor member 37a and a position adjuster 46 that slides the movable plates 37 on the basis of the position of the first floor member 37a so as to arrange the first floor member 37a on the irradiation area of the X-ray imaging devices 27.

When the X-ray generators 27a are installed in the rotating gantry 21a of full rotation type, the X-ray generators 27a rotate around the central axis in a substantially perfect circle.

Since the movable floor 24 moves along the support guides 26a, the movable floor 24 also forms a curved portion and a horizontal portion.

In this horizontal portion, the length of the movable floor 24 with respect to the central angle of rotation is shorter than the curved portion.

Thus, when the rotating gantry 21a and the movable plates 37 rotate at the same angular velocity, the circumferential angle of the particle beam irradiator 16 and the circumferential angle of the movable plate 37 are shifted.

In other words, in some cases the first floor member 37a having the circumferential angle difference of 45 degrees at a certain circumferential angle may deviate from the irradiation area of the X-ray generators 27a at another circumferential angle.

When the positional relationship between the first floor member 37a and the X-ray generators 27a is shifted, there are cases where the field of view of the X-ray image is narrowed or X-rays are shielded so that the X-ray image cannot be acquired.

When the circumferential angle difference of the particle beam irradiator 16 increases, the deviation becomes conspicuous.

For this reason, in consideration of the occurrence of such a shift in the horizontal portion, the first floor members 37a are usually provided on respective two or more adjacent movable plates 37.

However, even when the respective first floor members 37a are provided on two or more adjacent movable plates 37, the frames 43 shield the X-rays, and thus the marker and the characteristic bone portion cannot be properly specified in some cases.

Hence, at least a part of the movable floor 24 is not connected to the particle beam irradiator 16, and has a margin for sliding on the support guides 26a independently of the particle beam irradiator 16.

Figure 10:
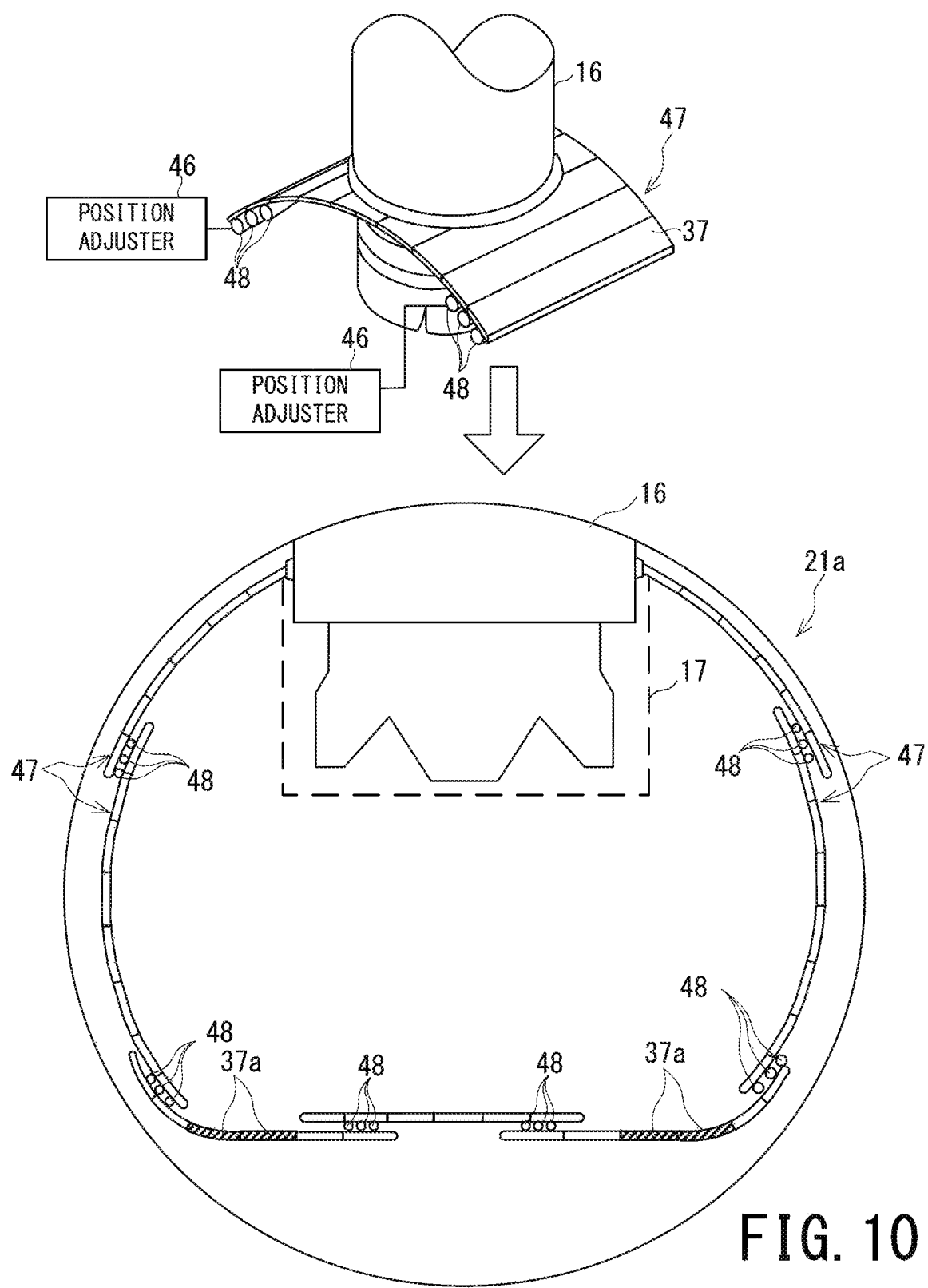
FIG. 10 is a schematic cross-sectional view of moving sheets included in the particle beam therapy apparatus according to the third embodiment.

FIG. 10 is a schematic cross-sectional view of moving sheets 47 provided in the treatment apparatus 10 according to the third embodiment.

Specifically, for instance, the movable plates 37 are divided into plural groups, each of which is composed of several movable plates 37 as shown in FIG. 10.

Adjacent movable plates 37 in each group are movably connected with each other while keeping a distance between them in such a manner that the respective group form plural moving sheets 47.

Each moving sheet 47 is overlapped at both ends on adjacent moving sheets 47, and one or more than one of the moving sheets 47 is engaged with the support guides 26a.

For instance, the support guides 26a are provided with two lanes composed of the inner-circumferential-side lane and the outer-circumferential-side lane (not shown).

The adjacent moving sheets 47 are alternately engaged with the inner-circumferential-side lane and the outer-circumferential-side lane.

Adjacent moving sheets 47 are slidably connected to each other with back rollers 48 in such a manner that each moving sheet 47 overlaps to the other moving sheet 47 at one end and overlaps the other moving sheet 47 adjacent at the other end for preventing occurrence of a gap.

In this manner, engaging the moving sheets 47 with the support guides 26a keeping the distance between centroids of the respective moving sheets 47 changeable within a margin makes it possible to match the circumferential angle of the particle beam irradiator 16 with the circumferential angle of the first floor member 37a.

Note that one or some of the plural moving sheets 47 is fixedly connected to the trunk of the particle beam irradiator 16.

The sensor 44 positioned at an immovable portion such as the base 22 is installed facing towards the moving sheets 47 engaged with each other in the above-described manner, and detects the positions of the respective first floor members 37a.

When the X-ray generators 27a are fixed to the rotating gantry 21a, the sensor 44 may be installed near the tip of the particle beam irradiator 16.

As a detection method, for instance, there is a method of sticking a fluorescent sticker to the frame 43 and optically detecting the reflection of the fluorescent sticker.

Further, instead of using the sensor 44, the relationship between the circumferential angle of the first floor member 37a and the circumferential angle at which the particle beam irradiator 16 stops may be memorized in advance so that the memorized relationship is used for calculating angle correction amount corresponding to the detected circumferential angle of the stopped position of the particle beam irradiator 16.

In any of the above-described cases, the information is sent to the position adjuster 46 and the position adjuster 46 performs correction processing such that the first floor member 37a positionally coincides to the irradiation area of the X-ray generators 27a.

In the calculation of the angle correction amount, it is preferable to perform the calculation such that the gap between the moving sheets 47 at the horizontal portion of the movable floor 24 becomes as small as possible.

This is because a gap is formed in the horizontal portion of the movable floor 24 when the angle correction amount exceeds the margin of the overlapped ends of the adjacent moving sheets 47.

Further, it is desirable to provide a guard such as a roll screen at each end of the moving sheets 47 in the horizontal portion in order to prevent small objects from dropping or getting caught when the gap is formed. Further, it is preferable to drive each moving sheet 47 so as not to generate a gap in the horizontal portion as much as possible.

The position adjuster 46 slides the moving sheets 47 on the basis of the relative circumferential angle between the FPDs 27b and the X-ray generators 27a so as to dispose the first floor member 37a on the irradiation area.

Since the X-ray generator 27a and the first floor member 37a can be made to coincide at an arbitrary circumferential angle as described above, it is possible to perform X-ray imaging from an arbitrary circumferential angle.

Figure 9:
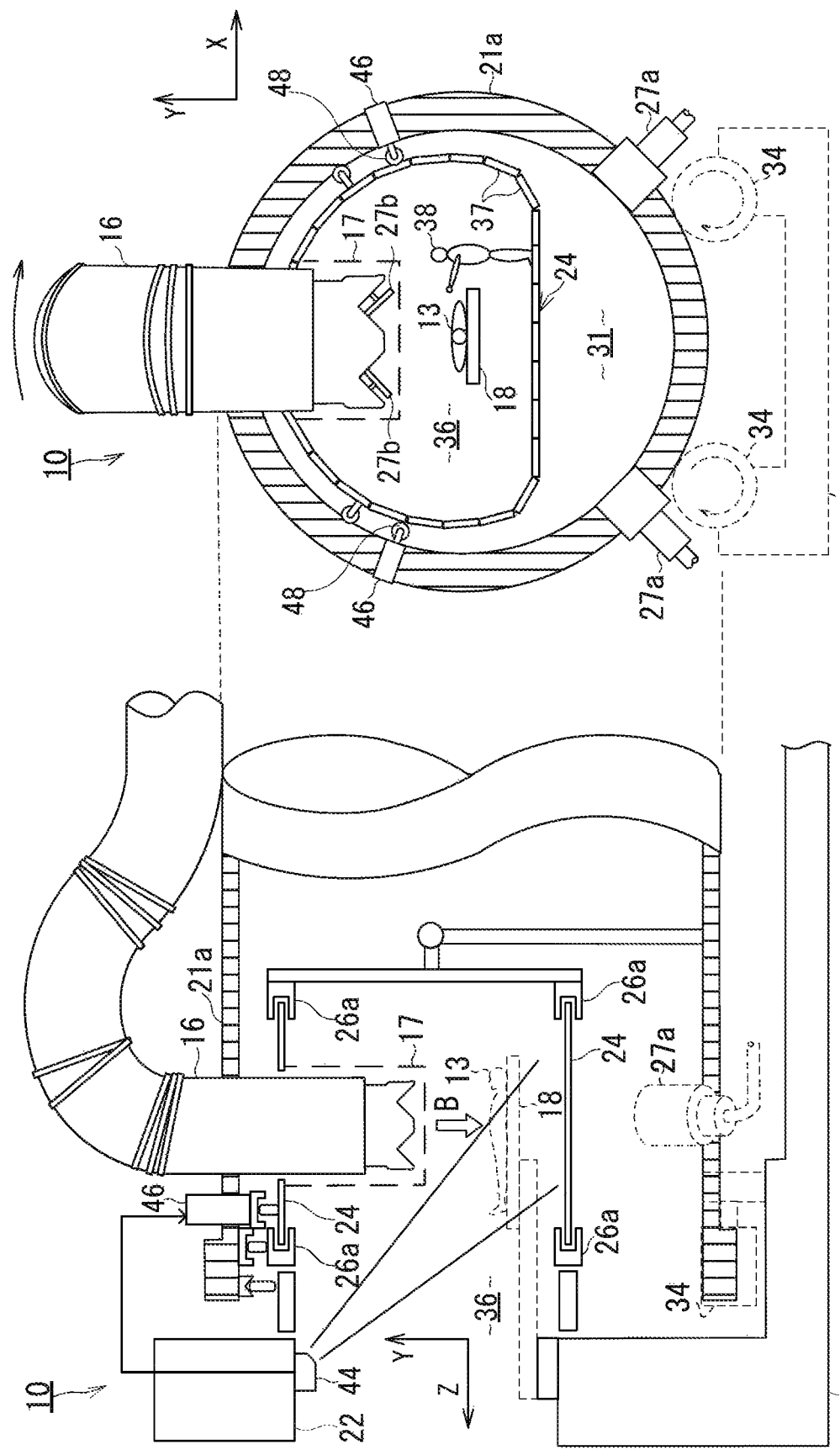
FIG. 9A is a cross-sectional view of the particle beam therapy apparatus according to the third embodiment, taken along the central axis of its rotating gantry.
FIG. 9B is a cross-sectional view of the particle beam therapy apparatus according to the third embodiment, taken along the direction perpendicular to the central axis of the rotating gantry.
Figure 12:
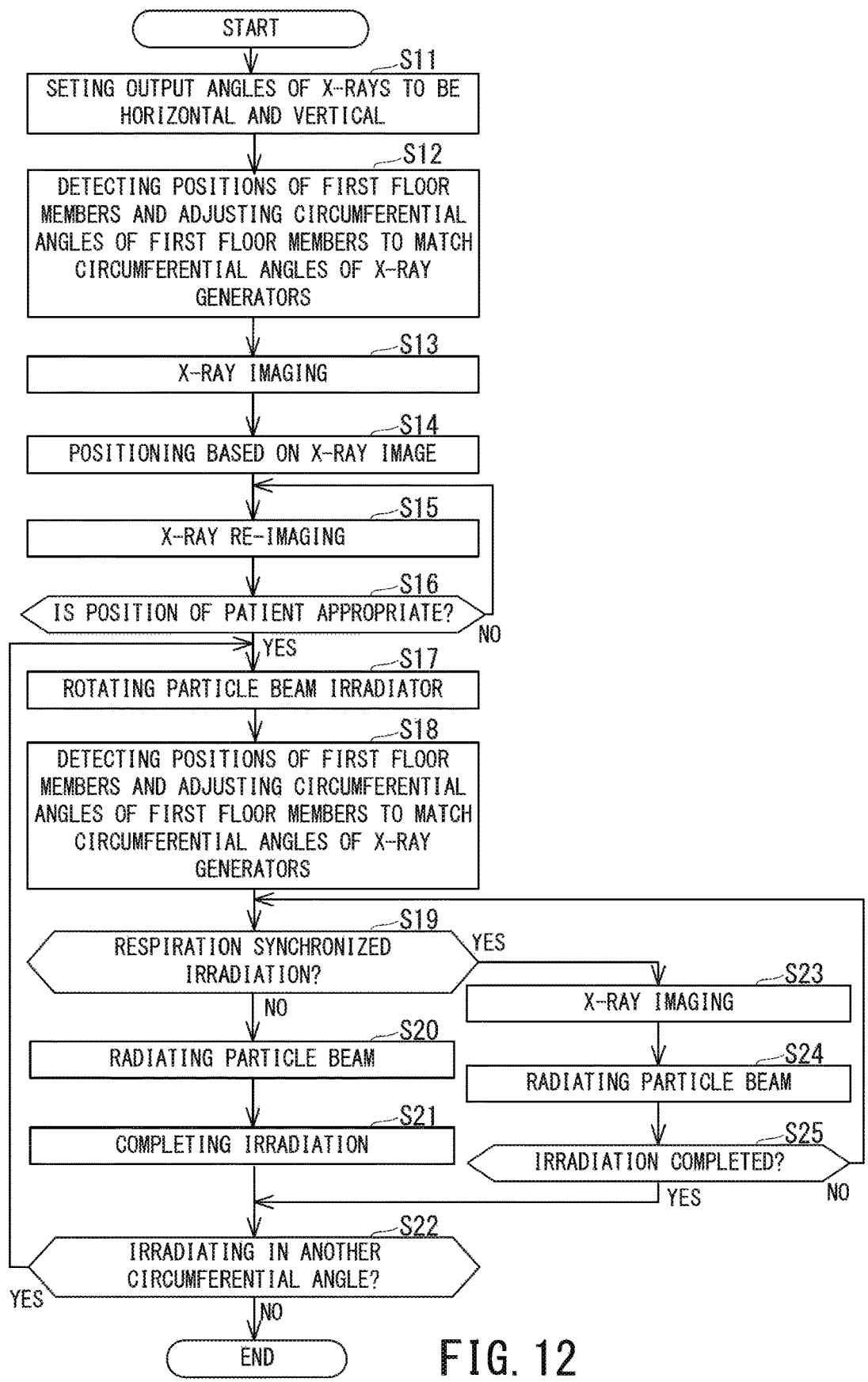
FIG. 12 is a flowchart illustrating an operation procedure of the particle beam therapy apparatus according to the third embodiment.

Next, the operation procedure of treatment apparatus 10 according to the third embodiment will be described on the basis of the flowchart of FIG. 12 by referring to FIG. 9 as required.

First, in the step S11, by setting the circumferential angle of the particle beam irradiator 16 to 45 degrees, the output directions of X-rays are set to the horizontal direction and the vertical direction.

In the next step S12, the respective positions of the first floor members 37a are detected by the sensor 44 and the respective circumferential angles of the first floor members 37a are adjusted so as to match the respective circumferential angles of the X-ray generators 27a.

In the next step S13, X-ray imaging is performed. In the X-ray imaging, X-rays pass through the first floor members 37a, further pass through the vicinity of the lesion area 19 of the patient 13, and are detected by the FPDs 27b fixed to the particle beam irradiator 16.

In the next step S14, the position of the patient 13 is adjusted on the basis of the acquired X-ray image in such a manner that the particle beam B can be accurately radiated onto the lesion area 19 having been set in treatment planning.

In the next step S15 after adjusting the position of the patient 13, X-ray imaging is performed again.

In the next step S16, a technician checks the X-ray image acquired in the step S15 and adjusts the position of the patient 13 based on the check result. The processing of the steps S15 and S16 is repeated until the position of the patient 13 becomes appropriate. Before and after the positioning, the technician 38 gets on the movable floor 24 to access the patient 13 in order to check the posture and condition of the patient 13 in some cases. When the position of the patient 13 is adjusted to an appropriate position, the positioning processing of the steps S15 and S16 is completed.

In the next step S17, the particle beam irradiator 16 is rotated and placed at the output position.

In the next step S18, the sensor 44 detects the respective positions of the first floor members 37a and the first floor members 37a are caused to slide such that the respective circumferential angles of the first floor members 37a match the respective circumferential angles of the X-ray generators 27a. When it is impossible to match the respective circumferential angles of the first floor members 37a with the respective circumferential angles of the X-ray generators 27a, it is sufficient that the first floor members 37a are included in the X-ray irradiation area.

In the next step S19, it is determined as to whether respiration synchronized irradiation is performed or not.

When it is determined in the step S19 that the respiration synchronized irradiation is not performed, the processing proceeds to the step S20 in which the particle beam irradiator 16 directly radiates the particle beam B.

In the next step S21 after irradiation of a predetermined dose according to the treatment plan, the irradiation is completed and the processing proceeds to the step S22.

In the next step S22, it is determined as to whether irradiation is performed by another circumferential angle or not. When the determination result is affirmative, the particle beam irradiator 16 is rotated and arranged at the next circumferential angle and the processing returns to the step S17. When the determination result is negative, i.e., irradiation by every circumferential angle in the treatment plan is completed, the particle beam therapy is completed.

In addition, there is a respiration synchronized irradiation method in which the particle beam B is radiated at a timing adjusted to the periodic displacement of the lesion area 19 due to respiration of the patient 13.

When it is determined in the step S19 that the respiration synchronized irradiation is performed, the processing proceeds to the step S23 in which X-ray imaging is performed for checking the position of the lesion area 19.

In the next step S24, when the lesion area 19 comes to the optimum position, the particle beam B is radiated at the adjusted timing such that X-ray imaging and irradiation of the particle beam B are repeated until it is determined in the next step S25 that the irradiation is completed.

After completion of the irradiation of the particle beam B at a specific circumferential angle, the processing proceeds to the step S22 in which the rotating gantry 21a is rotated so as to move the particle beam irradiator 16 to another circumferential angle similarly to the ordinary irradiation treatment method.

Since the respective circumferential angles of the first floor members 37a can be adjusted, it is possible to perform X-ray imaging for arbitrary times at a stopped circumferential angle without returning the particle beam irradiator 16 to the initial circumferential angle of 45 degrees.

Further, for instance, even when the physical condition of the patient worsens just before the beam irradiation and the patient once leaves the room and then returns to the treatment table again, X-ray imaging can be satisfactorily performed without returning the circumferential angle of the particle beam irradiator 16 to the initial angle (positioning angle), by adjusting the respective circumferential angles of the first floor members 37a in accordance with the circumferential angle of the stopped particle beam irradiator 16 as described above.

Position confirmation and treatment resumption can be performed in a short time without rotation of the particle beam irradiator 16 and without a drive system of the X-ray imaging devices.

Although the rotating gantry 21a of full rotation type has been described, the third embodiment can be similarly applied to the rotating gantry 21b of partial rotation type.

The particle beam therapy apparatus of the third embodiment has the same structure and the same operation procedure as those of the first embodiment except that the movable floor 24 is divided into moving sheets 47 and the stopped circumferential angle is corrected. Thus, duplicate description is omitted.

The same reference signs are assigned to the same components in terms of configuration or function as the first and second embodiments in each figure, and duplicate description is omitted.

According to the treatment apparatus 10 of the third embodiment as described above, in addition to the effect of the first embodiment, it is possible to match the X-ray generators 27a with the first floor members 37a at an arbitrary circumferential angle, and thus X-ray imaging can be performed at an arbitrary circumferential angle.

In addition, since it is unnecessary to return the circumferential angle of the particle beam irradiator 16 to the positioning angle (i.e., the circumferential angle at the start of the treatment) each time of X-ray imaging, the treatment time can also be shortened.

Since it is unnecessary to return the circumferential angle of the particle beam irradiator 16 to the positioning angle as described above, it is also possible to perform respiration synchronized irradiation or moving object tracking irradiation. The respiration synchronized irradiation is performed by synchronizing the shift of the lesion area 19 caused by breathing and/or change in posture of the patient 13 during irradiation of the particle beam, and the moving object tracking irradiation is performed by following the above-described shift of the lesion area 19.

Furthermore, since X-ray imaging can be performed from an arbitrary circumferential angle, X-ray irradiation can be performed from the optimum circumferential angle in relation to the lesion area 19.

Fourth Embodiment

FIG. 11A is a perspective view of the movable plates 37 of the treatment apparatus 10 according to the fourth embodiment.

FIG. 11B is a cross-sectional view taken along the line I-I in FIG. 11A, i.e., a cross-sectional view of the second floor member 37b.

FIG. 11C is a cross-sectional view taken along line II-II in FIG. 11A, i.e., a cross-sectional view of the first floor member 37a.

In the treatment apparatus 10 according to the fourth embodiment as shown in FIG. 11A, the first floor members 37a provided on two or more movable plates 37 adjacent to each other in the circumferential direction are continuously disposed without interposing the second floor member 37b between the first floor members 37a.

In other words, the first floor members 37a are continuously disposed in the circumferential direction without including the frames 43 (FIG. 6) shown in the first embodiment.

That is, each first floor member 37a is connected to the two parts of the second floor member 37b that is divided into the two parts along the circumferential direction.

In order to ensure the rigidity of each first floor member 37a, a rib (not shown) may be provided at each joint between the first floor member 37a and the second floor member 37b so as to join the first floor member 37a to the second floor member 37b.

(Condition of Transmission Path Length)

The continuously arranged first floor members 37a have, e.g., an L shape or a U shape so as to fit the shape of each second floor member 37b in some cases.

However, when X-rays pass through the first floor members 37a having such a shape, the transmission path length of X-rays changes abruptly and discontinuously in a case where the incident point of X-rays on the first floor members 37a and the incident angle of X-rays on the first floor members 37a continuously change.

In other words, when each first floor member 37a has a sharp shape such as a right-angled shape, due to a continuous change in relative angle between each first floor member 37a and each X-ray generator 27a, the transmission path length suddenly changes discontinuously.

Due to such a rapid change in transmission path length, there is a possibility that a steep peak recognized as an object is generated in the FPDs 27b.

For this reason, each first floor member 37a is formed into such a shape that the transmission path length of X-rays entering each first floor member 37a does not suddenly change even when the positional relationship between each first floor member 37a and each X-ray generator 27a changes.

For instance, as shown in FIG. 11C, it is desirable that each apex angle of each first floor member 37a is as smooth and gently bent as possible.

Further, the shape of each first floor member 37a is made as flat as possible to make the thickness of the first floor member 37a unchanged.

For instance, as can be understood by comparing FIG. 11B with FIG. 11C, it is preferable for each bent end portion of each first floor member 37a that the length of the bent portion is as short as possible.

In addition, each first floor member 37a preferably has such a shape that its length does not exceed the length determined as the allowable upper limit for X-rays made incident from an arbitrary relative position that the first floor member 37a and the X-ray generator 27a can take.

The particle beam therapy apparatus of the fourth embodiment has the same structure and the same operation procedure as those of the first embodiment except that the first floor members 37a are continuously arranged without providing the frames 43 and the shape of each movable plate 37 is defined. Thus, duplicate description is omitted.

The same reference signs are assigned to the same components in terms of configuration or function as the first to third embodiments in each figure, and duplicate description is omitted.

According to the treatment apparatus 10 of the fourth embodiment as described above, in addition to the effect of the third embodiment, X-ray imaging can be performed without using the sensor 44 and the position adjuster 46 for performing angle correction of the relative position between the movable floor 24 and each X-ray generator 27a.

According to the treatment apparatus 10 or the particle beam therapy method of at least one embodiment as described above, by providing the first floor member 37a on the movable plate 37, it is possible to acquire a high-quality X-ray image with a simple configuration and shorten the treatment time.

While certain embodiments have been described, these embodiments have been presented by way of example only, and are not intended to limit the scope of the inventions.

Indeed, the novel methods and systems described herein may be embodied in a variety of other forms; furthermore, various omissions, substitutions and changes in the form of the methods and systems described herein may be made without departing from the spirit of the inventions.

The accompanying claims and their equivalents are intended to cover such forms or modifications as would fall within the scope and spirit of the inventions.

The invention claimed is:

1. A particle beam therapy apparatus comprising:
a particle beam irradiator configured to output a particle beam;
a rotating gantry supporting the particle beam irradiator;
a moving floor including a plurality of moving plates along a circumferential direction of the rotating gantry and forming a horizontal portion below a top plate on which an object to be irradiated is to be placed;
an X-ray generator configured to generate X-rays; and
an X-ray detector detecting X-rays transmitted through the plurality of movable plates,
wherein at least one plate of the plurality of movable plates comprises:
a first floor member; and
a second floor member smaller in X-ray transmittance than the first floor member, and
wherein a material of the first floor member and a material of the second floor material are same, and thickness of the first floor member is thinner than thickness of the second floor member.

2. The particle beam therapy apparatus according to claim 1,
wherein the first floor member is removable from the moving floor.

3. The particle beam therapy apparatus according to claim 2,
wherein a size of a punched portion that is opened by removing the first floor member is larger than that of each X-ray generator.

4. The particle beam therapy apparatus according to claim 1,
wherein the first floor member is provided on all the moving plates at a same circumferential angle as the X-ray generator when the rotating gantry stops within its movable range.

5. The particle beam therapy apparatus according to claim 1, further comprising:
a position adjuster arranging the first floor member on an X-ray irradiation area according to an angle correction amount based on a relationship between a circumferential angle at which the particle beam irradiator stops and a circumferential angle of the first floor member.

6. The particle beam therapy apparatus according to claim 1,
wherein the moving plates are divided into a plurality of groups, and
wherein adjacent moving plates in one group are connected to form one moving sheet, and another moving sheet adjacent to moving sheet orbits in a different trajectory in a cross sectional view by a plane perpendicular to the rotation axis of the rotating gantry.

7. The particle beam therapy apparatus according to claim 1,
wherein the moving plates are divided into three or more groups, and the adjacent moving plates in one group are connected to form one moving sheet, and a distance between the first moving sheet adjacent to the particle beam irradiator and the second moving sheet not adjacent to the particle beam irradiator changes.

8. The particle beam therapy apparatus according to claim 1, further comprising:
a cover that covers a projection of the particle beam irradiator protruding from the rotating gantry into a treatment room,
wherein the X-ray detector is disposed inside the cover.

9. The particle beam therapy apparatus according to claim 1, further comprising:
a sensor detecting position of the first floor member.

10. A particle beam therapy apparatus comprising:
a particle beam irradiator configured to output a particle beam;
a rotating gantry supporting the particle beam irradiator;
a moving floor including a plurality of moving plates along a circumferential direction of the rotating gantry and forming a horizontal portion below a top plate on which an object to be irradiated is to be placed;
an X-ray generator configured to generate X-rays; and
an X-ray detector detecting X-rays transmitted through the plurality of movable plates,
wherein at least one plate of the plurality of movable plates comprises:
a first floor member; and
a second floor member smaller in X-ray transmittance than the first floor member, and
wherein the plate has a region in which a cross section perpendicular to a rotation axis of the rotating gantry is constituted only by the first floor member.

11. A plurality of moving plates constituting a moving floor that rotates along the circumferential direction, of a rotating gantry of a particle beam therapy apparatus, the plurality of moving plates comprising:
- at least one of the movable plates includes a first floor member transmitting X-rays detectably by a X-ray detector and a second floor member having a smaller X-ray transmittance than the first floor member,
- wherein the first floor member and the second floor member are a same material, and
- wherein thickness of the first floor member is thinner than thickness of the second floor member.

\* \* \* \* \*